United States Patent [19]

Sarrine

[11] Patent Number: 5,399,255
[45] Date of Patent: Mar. 21, 1995

[54] PLATFORM FOR CONDUCTING ELECTROPHORESIS, AND ELECTROPHORESIS PLATE FOR USE WITH THE PLATFORM

[75] Inventor: Robert J. Sarrine, Beaumont, Tex.

[73] Assignee: Helena Laboratories Corporation, Beaumont, Tex.

[21] Appl. No.: 86,916

[22] Filed: Jul. 7, 1993

Related U.S. Application Data

[63] Continuation-in-part of Ser. No. 79,229, Jun. 21, 1993, abandoned.

[51] Int. Cl.$^6$ .................. G01N 27/26; G01N 27/44
[52] U.S. Cl. .................. 204/299 R; 204/182.8
[58] Field of Search .................. 204/299 R, 182.8

[56] References Cited

U.S. PATENT DOCUMENTS

| | | | |
|---|---|---|---|
| 3,674,678 | 7/1972 | Post, Jr. et al. | 204/182.8 X |
| 4,360,418 | 11/1982 | Golias | 204/299 R |
| 4,391,689 | 7/1983 | Golias | 204/299 R X |
| 4,810,348 | 3/1989 | Sarrine et al. | 204/299 R |
| 4,827,780 | 5/1989 | Sarrine et al. | 204/299 R X |
| 4,874,491 | 10/1989 | Stålberg | 204/182.8 |
| 4,890,247 | 12/1989 | Sarrine et al. | 204/182.8 X |
| 4,892,639 | 1/1990 | Sarrine et al. | 204/299 R |
| 4,909,920 | 3/1990 | Sarrine et al. | 204/299 R |
| 4,938,080 | 7/1990 | Sarrine et al. | 204/299 R |
| 4,954,237 | 9/1990 | Sarrine et al. | 204/299 R |
| 4,975,173 | 12/1990 | Tansamrit et al. | 204/299 R |
| 5,045,164 | 9/1991 | Tansamrit et al. | 204/182.8 |

*Primary Examiner*—John Niebling
*Assistant Examiner*—John S. Starsiak, Jr.
*Attorney, Agent, or Firm*—Spencer, Frank & Schneider

[57] ABSTRACT

A platform for conducting electrophoresis includes a support, at least one first electrode which extends upward from the support, and at least one second electrode which also extends upward from the support. An electrophoresis plate is deposited on the support during a medical testing procedure. The electrophoresis plate includes a substrate and an electrophoretic medium layer on the substrate, the electrophoretic medium layer having first and second end regions. The at least one first electrode of the platform extends through a corresponding hole in the substrate to electrically contact the first end region of the electrophoretic medium layer and the at least one second electrode extends through a corresponding hole in the substrate to electrically contact the second end region of the electrophoretic medium layer. This arrangement makes it easy to install the electrophoresis plate on the platform and also provides good electrical contact with the electrodes. Holes are preferably provided in the first and second end regions of the electrophoretic medium layer above the holes in the substrate, and bubbles generated at the electrodes due to electrolytic decomposition of water in the electrophoretic medium layer escape through these holes. A bipolar power supply is preferably used in order to subdue arcing.

30 Claims, 4 Drawing Sheets

PLATFORM FOR CONDUCTING ELECTROPHORESIS, AND ELECTROPHORESIS PLATE FOR USE WITH THE PLATFORM

CROSS REFERENCE TO RELATED APPLICATION

This is a continuation-in-part of application Ser. No. 08/079,229, now abandoned entitled "Platform for Conducting Electrophoresis, and Electrophoresis Plate for Use with the Platform", filed Jun. 21st, 1993. The disclosure of this parent application is incorporated herein by reference.

BACKGROUND OF THE INVENTION

The present invention is directed in general to the field of electrophoretic analysis of liquid samples, such as biological specimens. More particularly, the invention is directed to a platform for conducting electrophoresis with an electrophoresis plate, and to the electrophoresis plate used with the platform.

Valuable information can be obtained by an analysis of certain biological fluids from a patient, such as blood serum, when diagnosing the patient's illness. Electrophoresis is known to be an effective technique for separating the various components of such fluid for subsequent analyses using optical densitometry techniques. The physical phenomenon underlying electrophoretic analysis is that particles which have an effective electric charge and which are deposited on a solid or semi-solid medium are caused to move with respect to the medium by an electric field applied across the medium. Particles of different types move at different rates, so a mixture of different types of particles is separated into its different components or fractions by electrophoretic analyses. These separated fractions may then be stained by exposing them to a suitable reagent so that the fractions can be optically detected using visible or ultraviolet light.

The electrophoresis process has been performed through a series of manual steps for many years. The manual process typically has started with the operator preparing an electrophoresis chamber by filling appropriate cavities of the chamber with buffer solution. Buffer solution is a liquid used in the electrophoresis process to maintain the surface of the electrophoretic medium in a moist condition and to provide an electrical interface to a power source applied to the chamber so that an electric field may be applied to the medium. The electrophoretic medium is typically a gel substance such as polyacrylamide or agarose that has been coated onto a Mylar (trademark) substrate to form an electrophoresis plate. The liquid sample to be examined is typically blood serum, but of course may be other liquids.

After the operator has prepared the electrophoresis chamber, he then applies consistent volumes of the samples to precise locations on the electrophoretic medium. The operator then places the medium into the electrophoresis chamber so that the edges of the medium are immersed in two buffer cavities at each of its longitudinal ends. Electrophoresis is then performed using a precise and consistent high voltage applied for a precise and consistent interval of time across the buffer cavities.

After electrophoresis has been completed, the operator applies a uniform coating of a staining reagent or stain to the surface of the medium, allowing a precise and consistent interval of time for the reagent and sample to chemically combine. The staining reagent is a liquid used after electrophoresis to chemically combine with the separated fractions of the fluid sample, causing the fractions to exhibit optical characteristics.

Next, the operator places the electrophoretic medium into a temperature-controlled oven and incubates it using a precise and consistent temperature and time interval. Incubation is the process of controlling the chemical reaction between the fractions of the liquid sample and the staining reagent by means of applying heat for a fixed interval of time.

Next, the operator dries the electrophoretic medium by increasing the oven temperature for a second precise and consistent temperature and time interval. The drying process steps the reaction between the separated fractions and the reagent by removing water from the medium. The medium can then be examined using optical densitometry techniques to determine which fractions were present in the original samples and to find their relative proportions.

The manual process described above requires careful attention by the operator in order to provide accurate and reproducible results. It is therefore not surprising that techniques for performing electrophoresis automatically have been developed. For example, U.S. Pat. Nos. 4,360,418 and 4,391,689 to Golias described an automated electrophoresis and staining apparatus and method. U.S. Pat. Nos. 4,810,348, 4,890,247, 4,909,920, and 4,954,237 to Sarrine et al also describe an automated electrophoresis apparatus and method. An automated applicator assembly with pipettes for transferring samples to the electrophoretic medium during automated analysis is described in U.S. Pat. Nos. 4,827,780 and 4,938,080 to Sarrine et al. All of these patents, which are assigned to the assignee of the present invention, are incorporated herein by reference.

SUMMARY OF THE INVENTION

An object of the invention is to provide an improved platform on which electrophoresis is conducted. A related object is to provide an improved electrophoresis plate for use on the platform.

In accordance with one aspect of the invention, the improved platform includes a support having a surface, at least a first electrode which extends upward from the surface, and at least a second electrode which also extends upward from the surface. The electrophoretic plate used with the platform includes a substrate and an electrophoretic medium layer on the substrate, the electrophoretic medium layer having first and second end regions. The electrophoresis plate has at least a first hole which extends through the substrate and at least a second hole which extends through the substrate. When the electrophoresis plate is installed on the platform, the first electrode of the platform extends through the first hole and the second electrode of the platform extends through the second hole of the electrophoresis plate. In a preferred form of this invention, plural electrodes and plural holes in the substrate and gel are provided.

In accordance with another aspect of the invention, an electrophoresis platform includes a support having a surface, a first electrode to electrically contact a first end region of an electrophoretic medium layer of an electrophoresis plate, a second electrode to electrically contact a second end region of the electrophoretic medium layer, and a bipolar power supply. The bipolar power supply provides the first electrode with an elec-

DESCRIPTION OF THE PREFERRED EMBODIMENTS

Figure 1:
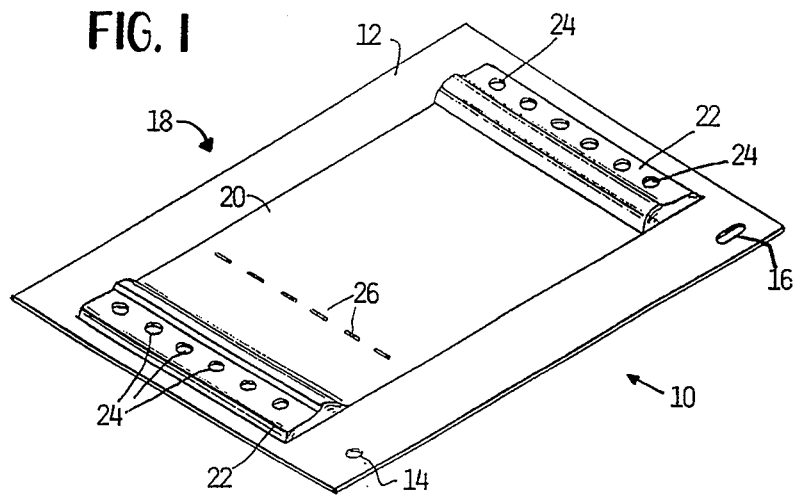
FIG. 1 a perspective view of an electrophoresis plate in accordance with the present invention.

FIG. 1 illustrates an electrophoresis plate 10 in accordance with the present invention that can be used with the electrophoresis platform of the present invention. Plate 10 includes a Mylar (trademark) substrate with a hole 14 and a slot 16 in it. Substrate 12 is 3⅜ inches wide and 4 15/16 inches long. Substrate 12 supports an electrophoretic medium layer 18 having a thin central region 20 between two mirror-image end regions 22. Central region 20 is approximately 16/1000 inches thick and end regions 22 are substantially thicker, as shown. Electrophoretic medium layer 18 is a gel-like layer which includes agarose, water, and a buffer. The agarose provides a micro-porous support which has tiny pores that contain the water, and the buffer serves as an electrolyte which renders the water electrically conductive.

Each end region 22 has at least one and, as illustrated, six holes 24 which extend through the agarose and the substrate 12. Central region 20 has six wells 26. Wells 26 are elongated depressions in the agarose of central region 20 and do not extend through substrate 12.

Plate 10 may be used, for example, to confirm a diagnosis of myocardial infarction. In a typical situation serum drawn from the patient at hourly intervals would be placed in three of the wells 26. A reference/calibrator fluid, a normal control fluid, and an abnormal control fluid would be placed in the other three wells 26. Electrophoresis would then be conducted by establishing a DC electric field from one end region 22 to the other end region 22, causing different fractions in the fluids to travel through the agarose at different rates. Following electrophoresis the plate 10 would be treated with a reagent and dried in order to make the dispersed fractions fluoresce under ultraviolet light.

From the above description of microphoresis plate 10 it would be apparent that the term "plate" does not imply a rigid structure. Plate 10 is, instead, moderately flexible. Further information about plate 10 and its fabrication can be found in an application by Philip A. Guadagno et al entitled "Electrophoresis Plate Having A Hydroscopic Agent," filed concurrently herewith under attorneys' docket HELAB 0297.

Figure 2:
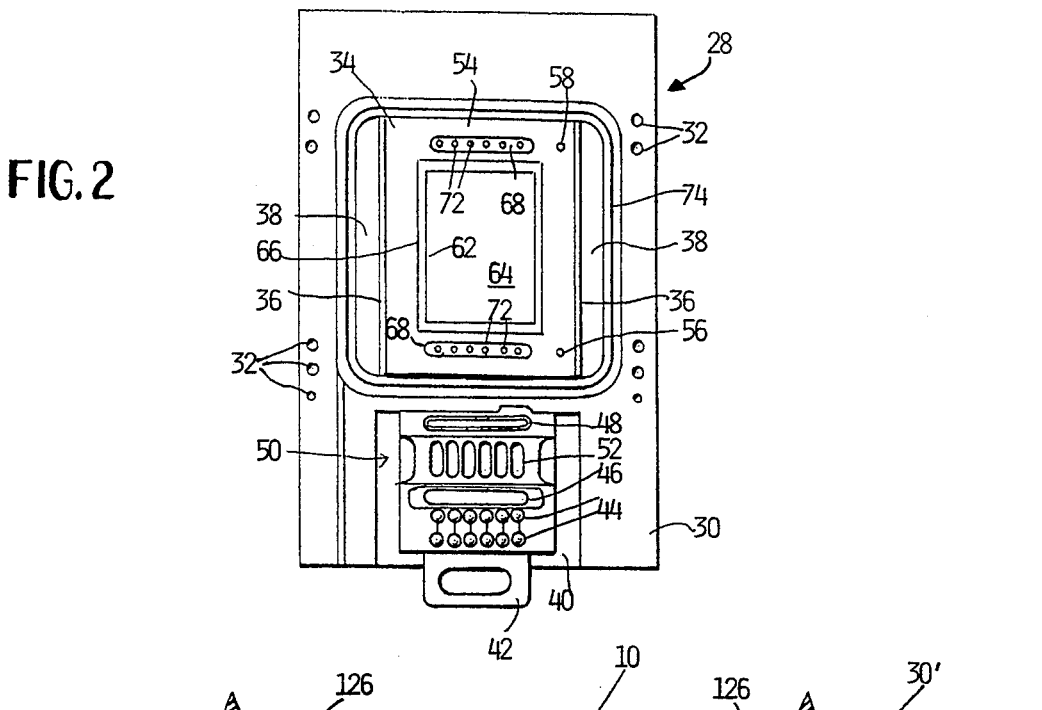
FIG. 2 is a top plan view of an electrophoresis platform in accordance with the present invention, FIG. 2 additionally showing a sample tray on the platform.

FIG. 2 illustrates a view of an electrophoresis platform 28 from the top. Platform 28 includes a plastic tray 30 on which plate 10 is supported during electrophoresis. Tray 30 has holes 32 adjacent its longitudinal edges for accommodating mounting screws (not illustrated). Tray 30 also has a recessed region 34 with two ribs 36 in it. Outward of ribs 36 are troughs 38.

Tray 30 additionally has a recessed region 40 for accommodating a sample tray 42. Sample tray 42 has two rows of wells 44. There are six wells 44 in each of those rows, and either row of wells can be used to hold the six samples that are to be transferred to the wells 26 of electrophoresis plate 10 (see FIG. 1). Sample tray 42 also has troughs 46 and 48 for cleaning solutions and a region 50 with six elongated depressions 52 in it. During use six pipettes (not illustrated) of an applicator assembly (not illustrated) transfers samples from the wells 44 to the wells 24 (see FIG. 1) and are washed with solutions from troughs 46 and 48. A strip of blotting paper (not illustrated) is placed on the region 50. The depression 52 permits the pipettes to be driven downward into contact with the paper to blot them during the washing procedure without the risk of damage to the pipettes.

A ceramic frame 54 is mounted in recessed region 34 of tray 30. Frame 54 has two holes through which extend pegs 56 and 58 that are part of tray 30. The holes through which pegs 56 and 58 extend are not numbered in FIG. 2 (but bear reference number 60 in FIG. 3). Plate 54 also has a rectangular opening 62. A copper heat-transfer member 64 protrudes into opening 62. A thin Mylar (trademark) film 66 is adhesively attached to member 64 and to frame 54 at the periphery of opening 62 in a sealing manner, and protects member 64 from fluid. Finally, frame 54 has two elongated slots which expose conductive members 68. These slots are not numbered in FIG. 2 (but bear reference number 70 in FIG. 3). Conductive members 68 are made of compressed graphite and each has at least one and, as illustrated, six electrodes 72.

A resilient sealing member 74 is mounted on tray 28 around recessed region 34. Member 74 is preferably a flexible strip of the type used in windshield wipers.

During use, a liquid surfactant is swabbed onto film 66 to promote good thermal transfer. An electrophoresis plate 10 as shown in FIG. 1 is then deposited in recessed region 34 of the tray 30, with the longitudinal edges of substrate 12 abutting ribs 36. Peg 56 extends through hole 14 and peg 58 extends through slot 16 to precisely orient the electrophoresis plate 10 with respect to tray 30. Additionally, electrodes 72 extend through holes 24 and make electrical contact with the agarose.

Figure 3:
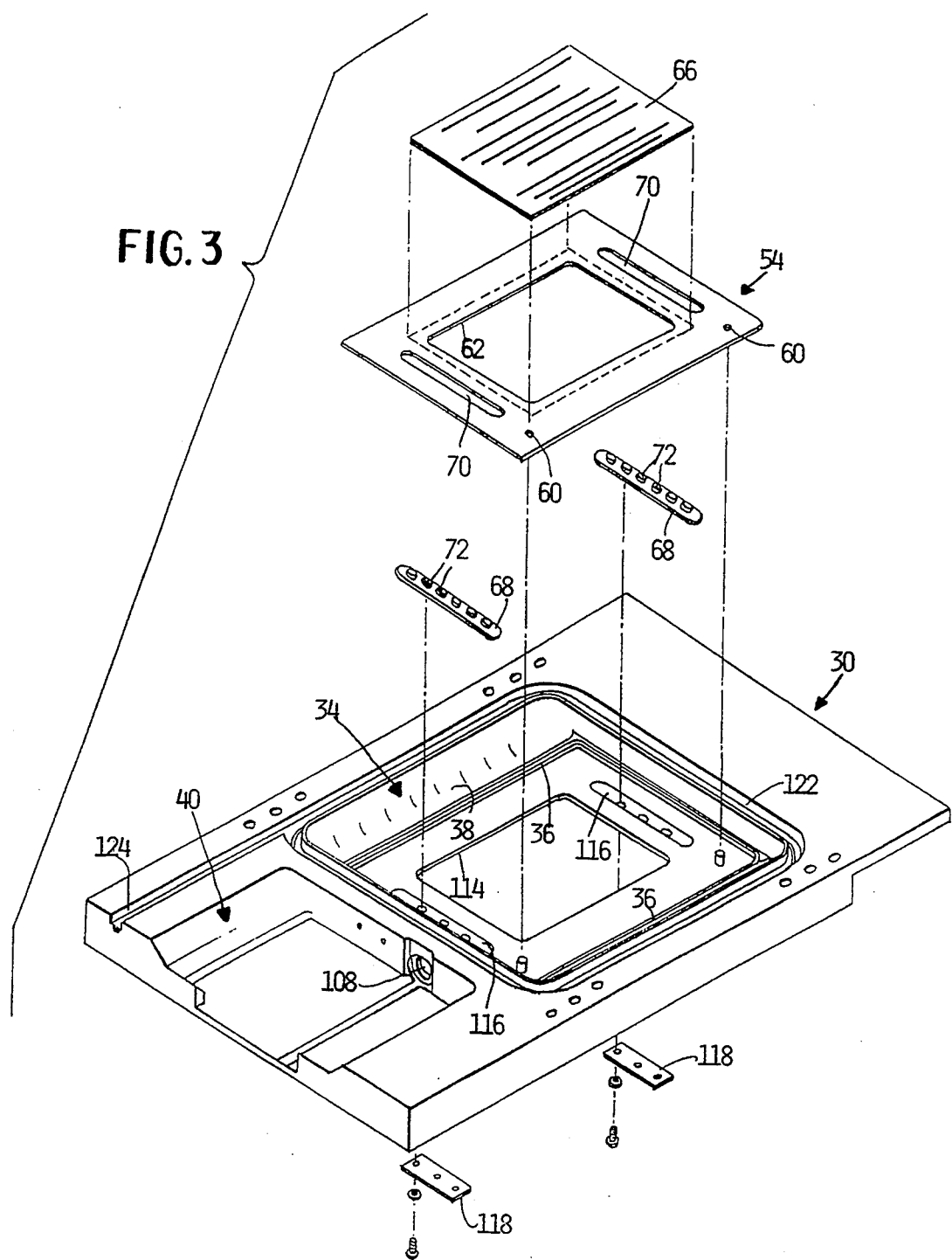
FIGS. 3 and 4 together provide an exploded perspective view of the electrophoresis platform shown in FIG. 2.
Figure 4:
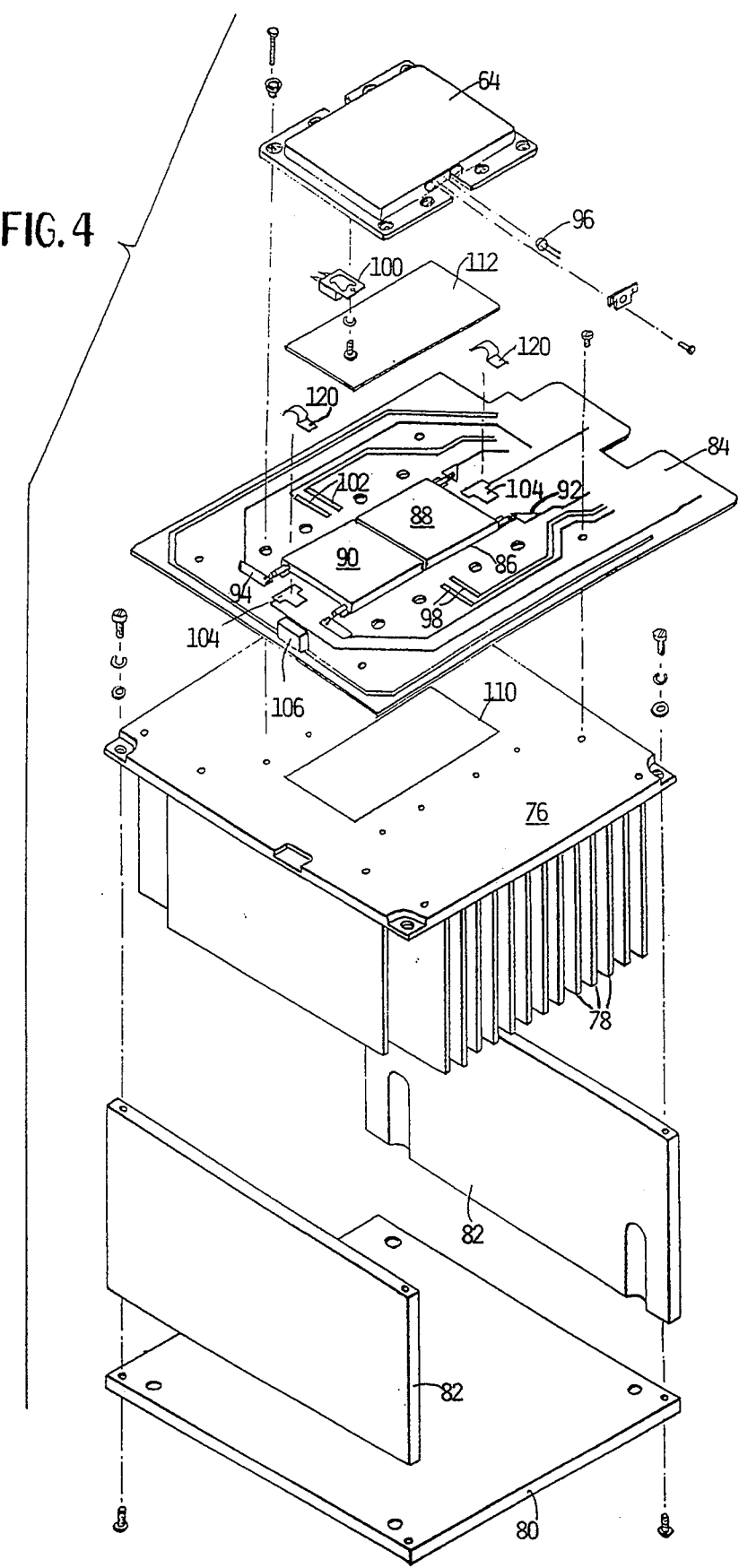

Turning next to FIGS. 3 and 4, electrophoresis platform 28 also includes a heat sink 76 which is made from extruded aluminum and which includes cooling fins 78. Heat sink 76 is mounted on a support 80 by way of walls 82, which are screwed to both heat sink 76 and support 80. A printed circuit board (PCB) 84 has conductor patterns on both its top and bottom surfaces (although the pattern on the bottom surface is not shown in the drawings). Plated-through holes, not shown, are used to make electrical connections between the conductors on the top surface and the bottom surface. PCB 84 has a central rectangular opening 86 through it. Peltier devices 88 and 90 are mounted in the opening 86, with Peltier device 88 being soldered to conductive regions 92 on PCB 84 and with Peltier device 90 being soldered to conductive regions 94. A temperature detector 96 is soldered to conductive regions 98 and an over-temperature circuit breaker 100 is soldered to conductive regions 102. The case of temperature detector 96 is electrically grounded. Conductive regions 104 are also part of the conductor pattern on the upper surface of PCB 84 and their use will be explained later. An optical sensor 106 is soldered to the conductor pattern to detect, through an opening 108 in tray 30, whether sample tray 42 (FIG. 2) is present in recessed region 40.

The conductor pattern on the bottom surface of PCB 84 is covered with an insulating layer (not shown). Furthermore, a film 110 of heat transfer compound is disposed on the upper surface of heat sink 76 between the Peltier devices and the heat sink. Film 110, which is pliable and conforms to any surface irregularities that may be present on heat sink 76 and the Peltier devices, is available from Berkuest Company under the designation SX-Q2. PCB 84 is screwed to the top surface of heat sink 76, and a dab of heat-transmitting jelly (not illustrated) may additionally be used between the Peltier devices and film 110. Another film 112 of heat transfer compound is disposed between Peltier devices 88 and 90 and heat-transfer member 64, which is screwed to heat sink 76 through openings in PCB 84. Heat-transfer gel (not illustrated) may also be applied to the bottom surface of member 64 and the top surfaces of Peltier devices 88 and 90. Sensor 96 and circuit breaker 100 are mounted on member 64.

With continuing reference to FIGS. 3 and 4, heat-transfer member 64 extends through an opening 114 in tray 30 and is positioned so that its top surface is even with the top surface of ceramic frame 54. Conductive members 68 are lodged in elongated recesses 116 in tray 30 and are screwed to metal straps 118 through screw holes (not numbered) at the bottom of recesses 116. Straps 118 are positioned to make electrical contact with contact springs 120 which are soldered to the conductive regions 104 on PCB 84. In this way, high voltage can be transferred to electrodes 72 via PCB 84 without soldered connections between conductive members 68 and PCB 84. This not only facilitates assembly of platform 28, it also permits tray 30 to be unscrewed and simply lifted away from PCB 84 during replacement of conductive members 68.

After conductive members 68 have been mounted on tray 30 and frame 54 has been installed, film 66 is adhesively applied as previously discussed.

Tray 30 has a channel 122 around recessed region 34 to receive resilient sealing member 74 (FIG. 2). A lead-in channel 124 is provided in tray 30 to permit member 74 to be threaded into channel 122 during assembly.

Figure 5:
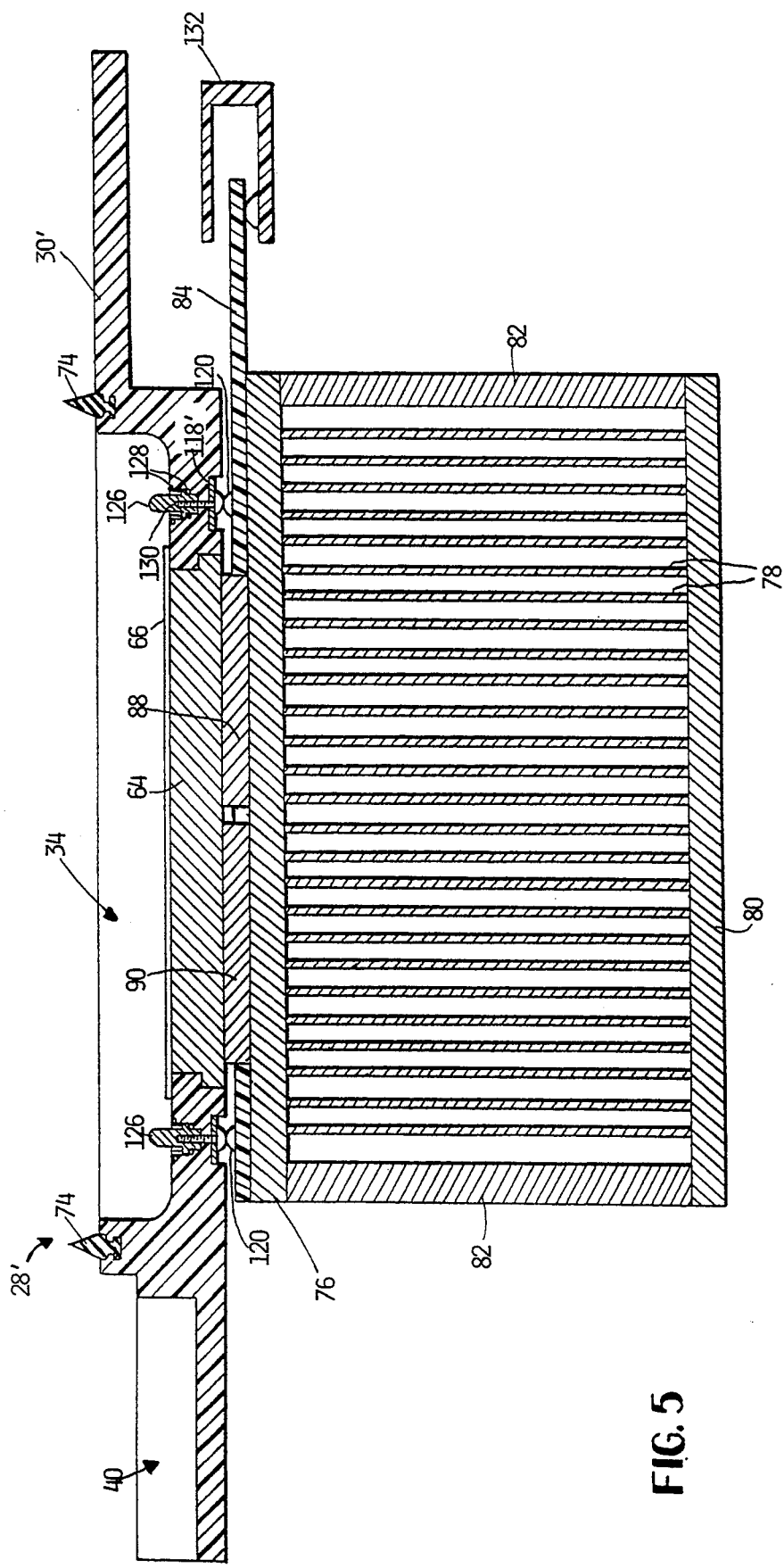
FIG. 5 is a sectional view of electrophoresis platform in accordance with a modified embodiment of the present invention, and additionally shows an electrical receptacle which cooperates with the platform when the platform is at a predetermined position.

FIG. 5 illustrates a cross-sectional view of a platform for conducting electrophoresis in accordance with a modified embodiment of the present invention. The electrophoresis platform 28' shown in FIG. 5 is the same as platform 28 of the first embodiment except that it does not include a ceramic plate 54, twelve individual electrodes 126 are used rather than two conductive members 68 having six electrodes 72 each, and the tray 30' of platform 28' is modified to accommodate individual electrodes 126 rather than conductive members 68. Insulating films 110 and 112 (see FIG. 4) are present in the modified embodiment but are not shown in FIG. 5 to facilitate convenient illustration.

In FIG. 5, each electrode 126 is deposited in respective a blind bore (not numbered) in tray 30' and is sealed by a pair of O-rings 128. Each electrode 126 has a threaded bore (not numbered) which receives a screw 130 extending through an opening in a strap 118'. Contact springs 120 on PCB 84 make electrical contact with the head of one of the screws 130 at each end. Electrodes 126 are made of compressed graphite.

Although not shown in the drawings, most of the conductor patterns on PCB 84 are always electrically connected to external circuitry which receives signals from sensors 96, 100, and 106 (FIG. 4) and which supplies power to Peltier devices 88 and 90 (FIG. 4). Conductive regions 104 (FIG. 4), in contrast, are not always electrically connected to an external circuitry. FIG. 5 schematically illustrates a receptacle 132 which electrically contacts conductor patterns on PCB 84 that are connected to conductive regions 104 when electrophoresis platform 28 is in an withdrawn position. Accordingly, high voltage is supplied to electrodes 126 (and electrodes 72 in the first embodiment) only when the electrophoresis platform is in the withdrawn position.

Figure 6:
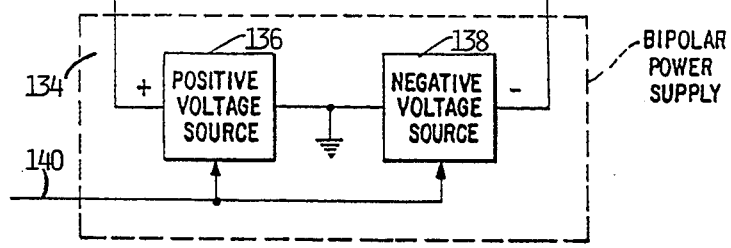
FIG. 6 is a sectional view showing a bipolar power supply connected to the electrodes of the electrophoresis platform of the embodiment shown in FIG. 5.

FIG. 6 illustrates the electrical connection to the electrodes 126 when an electrophoresis plate 10 is installed in tray 30' and the electrophoresis platform is in its withdrawn position. Various features of the electrophoresis platform, such as heat sink 76 and PCB 84, are not shown in FIG. 6.

A bipolar power supply 134 includes a positive voltage source 136 and a negative voltage source 138 which are connected in series. Source 136 supplies a potential which is positive with respect to ground to the electrodes 126 at one end of electrophoresis plate 10, while source 138 supplies a potential that is negative with respect to ground to the electrodes 126 at the other end of plate 10. Sources 136 and 138 receive a control signal over a conductor 140 to set the total potential difference provided by power supply 134.

Typical values for the current and voltage supplied across plate 10 during rapid electrophoresis are 30 milliamps and 1500 volts, respectively. This represents 45 watts dissipated by plate 10. The resulting heat is transferred via heat-transfer member 64 and Peltier devices 88 and 90 to heat sink 76. During portions of the electrophoresis procedure (i.e., incubation and drying) the current through Peltier devices 88 and 90 is reversed to help heat plate 10. During electrophoresis a cover member (not illustrated) engages resilient sealing member 74 to form an electrophoresis chamber together with the electrophoresis platform.

During electrophoresis, the electrolytic decomposition of water in agarose layer 18 (see FIG. 1) of plate 10 causes bubbles of hydrogen gas to form at the electrodes 126 connected to source 138 and oxygen bubbles to form at the electrodes 126 connected to source 136. The fact that holes 24 (see FIG. 1) extend all the way through end regions 22 (see FIG. 1) of plate 10 permits these bubbles to escape. It might appear desirable to increase the total area of contact between electrodes 126 and the agarose of end regions 22 by configuring end regions 22 so that the agarose completely covers electrodes 126 (i.e., by modifying holes 124 so that they do not go all the way through, and are instead closed at their top ends), but this would allow the gases of electrolytic decomposition to accumulate under plate 10 and lift it away from tray 30' and electrodes 126, thus undermining the accuracy of the optical measurements following the electrophoresis procedure.

The use of a bipolar power supply (e.g., 134) means that, during electrophoresis, none of the electrodes 126 is different from ground potential by more than half of the voltage across electrophoresis plate 10. That is, to obtain 1500 volts across plate 10, source 136 is set at +750 volts and source 138 is set at −750 volts, so that neither set of electrodes 126 differs from ground potential by the full 1500 volts. This reduces or avoids entirely damage due to arcing. The electrophoresis platform 28 of the first embodiment has increase protection for whatever arcing might occur even with bipolar power supply 134 since it employs ceramic plate 54. Although plate 54 is used in a damp environment and thus does little to increase the electrical isolation between the electrodes and heat-transfer member 64, for example, it is tough and prevents the heat of an arc from charring the plastic of tray 30.

The ceramic from which plate 54 is made is a machinable ceramic which is available from Dow Chemical Company under the trademark "Macor." The ceramic is baked in a billet and sliced. The holes 60, opening 62, and slots 70 (see FIG. 3) are then machined into a slice.

The present invention does not require that the number of wells 26 corresponds to the number of electrodes. Furthermore it is within the scope of this invention that the electrodes may create or form the holes in the gel when the gel is placed on the platform.

It will be understood that the above description of the present invention is susceptible to various modifications, changes and adaptations, and the same are intended to be comprehended within the meaning and range of equivalents of the appended claims.

What is claimed is:

1. A platform for conducting electrophoresis with an electrophoresis plate which includes a substrate and an electrophoretic medium layer with first and second end regions on the substrate, said platform comprising:
   support means, having a surface, for supporting the substrate of the electrophoresis plate on the surface, and including a plastic tray having a recessed region with a bottom portion and an opening in the bottom portion, and a heat-transfer member which protrudes into the opening;
   a first electrode extending upwardly from the surface of the support means to contact the first end region of the electrophoresis plate, the first electrode being mounted on the bottom portion adjacent the opening; and
   a second electrode extending upwardly from the surface of the support means to contact the second end region of the electrophoresis plate and being mounted on the bottom portion adjacent the opening, the electrophoresis plate being supported above the heat-transfer member and regions of the bottom portion adjacent the opening.

2. The platform of claim 1, further comprising at least one additional first electrode extending upwardly from the surface of the support means to contact the first end region of the electrophoresis plate.

3. The platform of claim 2, further comprising at least one additional second electrode extending upward from the surface of the support means to contact the second end region of the electrophoresis plate.

4. The platform of claim 3, wherein at least one of the second electrodes is part of an elongated conductive member.

5. The platform of claim 3, wherein at least one of the second electrodes is an individual electrode which is spaced apart from every other second electrode.

6. The platform of claim 1, wherein the support means further comprises a ceramic plate disposed in the recessed region of the bottom portion of the tray, the ceramic plate having at least one first opening through which the first electrode extends, at least one second opening through which the second electrode extends, and a central opening between the at least one first opening and the at least one second opening, the heat-transfer member protruding through the opening in the bottom portion of the recessed region of the tray and into the central opening in the ceramic plate.

7. The platform of claim 1, further comprising a printed circuit board below the tray, the printed circuit board having a first conductive region for supplying electrical power to the first electrode and a second conductive region for supplying electrical power to the second electrode, a first spring contact to electrically connect the first conductive region to the first electrode, and a second spring contact to electrically connect the second conductive region to the second electrode.

8. The platform of claim 7, further comprising an electrical receptacle which receives the printed circuit board when the printed circuit board is in a predetermined position and which transfers electrical power to the first and second conductive regions on the printed circuit board only when the printed circuit board is in the predetermined position.

9. The platform of claim 8, further comprising a bipolar power supply which is connected to the first and second conductive regions on the printed circuit board when the printed circuit board is in the predetermined position.

10. The platform of claim 7, wherein the printed circuit board has an opening, and further comprising at least one Peltier device in the opening adjacent the heat-transfer member, and a heat sink below the printed circuit board adjacent the at least one Peltier device.

11. The platform as defined in claim 1, wherein the first electrode is configured to form a cavity in the first end region of the electrophoresis plate.

12. The platform as defined in claim 1, wherein the first and second electrodes are configured to form cavities in the first and second end regions of the electrophoresis plate.

13. The platform of claim 1, wherein the surface of the support means which supports the substrate of the electrophoresis plate is flat.

14. A platform for conducting electrophoresis with an electrophoresis plate which includes a substrate and an electrophoretic medium layer with first and second end regions on the substrate, said platform comprising:
   support means, having a surface, for supporting the substrate of the electrophoresis plate on the surface;
   a first electrode extending upwardly from the surface of the support means to contact the first end region of the electrophoresis plate;
   a second electrode extending upwardly from the surface of the support means to contact the second end region of the electrophoresis plate; and
   bipolar power supply means for supplying the first electrode with an electrical potential that is positive with respect to ground potential and for supplying the second electrode with an electrical potential that is negative with respect to ground potential.

15. An electrophoresis plate comprising:
   a substrate;
   a separation region including gel material in contact with the substrate;

two spaced-apart end regions each including gel material and electrode buffer material; and the substrate including at least two apertures, each aligned under one of the end regions.

16. The electrophoresis plate of claim 15, wherein at least one electrode receiving cavity is formed in each of said end region.

17. The electrophoresis plate of claim 15, wherein the end regions are in contact with the substrate.

18. An electrophoresis plate for use with an electrophoresis platform which includes support means for supporting the electrophoresis plate on a surface, at least one first electrode extending upward from a first region of the surface of the support means, and at least one second electrode extending upward from a second region of the surface of the support means, the first and second regions of the surface of the support means being spaced apart, said electrophoresis plate comprising:

a substrate having at least one first hole for receiving the at least one first electrode and at least one second hole for receiving the at least one second electrode;

an electrophoretic medium layer on the substrate, the electrophoretic medium layer having a first end region to receive the at least one first electrode and a second end region to receive the at least one second electrode; and at least one pre-formed cavity in at least one end region extending entirely through the end region.

19. The electrophoresis plate of claim 18, wherein the electrophoresis platform further includes at least one additional first electrode and at least one additional second electrode, and wherein the substrate further includes at least one additional first hole to receive the at least one additional first electrode and at least one additional second hole to receive the at least one second electrode.

20. The electrophoresis plate of claim 18, wherein the at least one pre-formed cavity receives an electrode therein.

21. The electrophores is plate of claim 18, wherein the electrophoretic medium layer comprises agarose.

22. A platform for conducting electrophoresis with an electrophoresis plate which includes a substrate and an electrophoretic medium layer with first and second end regions on the substrate, comprising:

support means, having a surface, for supporting the electrophoresis plate on the surface;

a first electrode to electrically contact the first end region of the electrophoretic medium layer;

a second electrode to electrically contact the second end region of the electrophoretic medium layer; and a polar power supply means for supplying the first electrode with an electrical potential that is positive with respect to ground potential and for supplying the second electrode with an electrical potential that is negative with respect to ground potential.

23. The platform of claim 22, further comprising at least one additional first electrode and at least one additional second electrode, the first electrodes extending upward from the surface of the support means and the second electrodes extending upward from the surface of the support means.

24. The platform of claim 23, wherein the first electrodes are part of an elongated conductive member, the elongated conductive member being mounted on the bottom portion of the recessed region of the tray.

25. The platform of claim 22, wherein the support means comprises a plastic tray having a recessed region with a bottom portion and an opening in the bottom portion, and a heat-transfer member which protrudes into the opening, the first electrode being mounted on the bottom portion adjacent the opening and the second electrode being mounted on the bottom portion adjacent the opening, the electrophoresis plate being supported above the heat-transfer member and regions of the bottom portion adjacent the opening.

26. The platform of claim 25, wherein the first electrodes are individual electrodes which are mounted at spaced-apart positions on the bottom portion of the recessed region of the tray and which are electrically connected together.

27. The platform of claim 25, wherein the support means further comprises a ceramic plate disposed in the recessed region of the bottom portion of the tray, the ceramic plate having at least one first opening through which the first electrode extends, at least one second opening through which the second electrode extends, and a central opening between the at least one first opening and the at least one second opening, the heat-transfer member protruding through the opening in the bottom portion of the recessed region of the tray and into the central opening in the ceramic plate.

28. The platform of claim 25, further comprising a printed circuit board below the tray, the printed circuit board having a first conductive region for supplying electrical power to the first electrodes and a second conductive region for supplying electrical power to the second electrodes, a first spring contact to electrically connect the first conductive region to the first electrodes, and a second spring contact to electrically connect the second conductive region to the second electrodes.

29. An electrophoresis plate comprising:
a separation region including gel material;
two spaced-apart regions including gel material and electrode buffer material, each end region including at least one hollow electrode receiving cavity formed therein; and
a substrate with a flat surface, the separation region and the spaced-apart regions being supported on the flat surface of the substrate.

30. The electrophoresis plate of claim 29, wherein the substrate includes at least one aperture aligned relative to an end region.

* * * * *